March 22, 1955 A. MANSUINO Plant Pat. 1,366
ROSE PLANT
Filed July 27, 1954
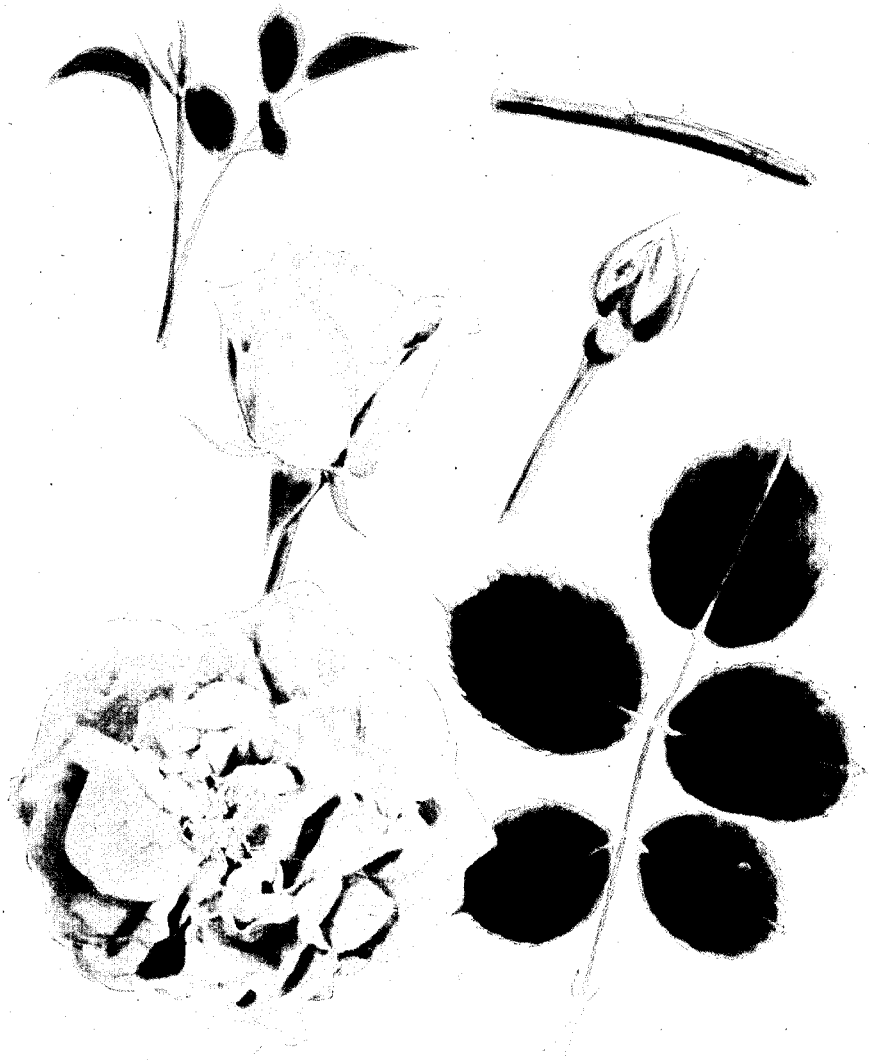
Inventor.
Ada Mansuino
By: Robb & Robb
Attorneys.

United States Patent Office

Plant Pat. 1,366
Patented Mar. 22, 1955

1,366

ROSE PLANT

Ada Mansuino, San Remo, Italy, assignor to Jackson & Perkins Company, Newark, N. Y., a corporation of New York Application July 27, 1954, Serial No. 446,189

1 Claim. (Cl. 47—61)

The present invention relates to a new and distinct variety of rose plant of the climber class, which was originated by me by crossing the climbing tea "Reine Marie Henriette" variety (unpatented) with an unnamed and unpatented seedling of "Paul's Scarlet" climber.

The primary objective in making this cross was to produce a new, large-flowered, remontant, red climbing rose. This objective was fully achieved, as evidenced by the fact that my new variety is particularly characterized by its climbing habit, as indicated from the fact that the plants usually attain a height of from 8 to 10 feet tall, its large, hybrid tea size flowers of a distinctive deep red general color tonality, the strong Old Rose fragrance of its flowers, and its glossy dark green foliage. These characteristics definitely distinguish my new variety from its parents, as well as from all other varieties of its class.

Asexual reproduction of my new variety by budding, as performed at Newark, New York, and also at Pleasanton, California, shows that the foregoing characteristics and distinctions come true to form and are established and transmitted through succeeding propagations.

The accompanying drawing shows typical specimens of the flowers, foliage and stems of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—Climbing tea "Reine Marie Henriette."
- *Pollen parent.*—An unnamed seedling of "Paul's Scarlet" climber.

Classification:
- *Botanic.*—Climber.
- *Commercial.*—Climber.

FLOWER (Observations made from specimens grown outdoors at Newark, New York, in the latter part of the month of July, and in the early morning.)

Blooming habit: Recurrent—continuous.

Bud:
- *Size.*—Large.
- *Form.*—Globular; is not affected by wet or hot weather.
- *Color.*—When sepals first divide—Victoria Lake, Plate 1. When petals begin to unfurl—Carmine, Plate 1. When half blown: Inside of petals—Carmine, Plate 1, lightly overcast with Spectrum Red, Plate 1; reverse of petals—Spectrum Red, Plate 1, lightly overcast with Carmine, Plate 1.
- *Sepals.*—Slightly branched; curl back when petals begin to unfurl. Color: Inside—Olivine, Plate 32; outside—Absinthe Green, Plate 1.
- *Calyx.*—Color—Light Cress Green, Plate 31. Shape—pear. Size—small. Aspect—smooth. Odor when rubbed—none.
- *Peduncle.* — Length—medium. Aspect—smooth. Strength—erect; slender. Color—Deep Dull Yellow-Green, Plate 32.
- *Opening.*—Opens up well; is not affected by adverse weather conditions.

Bloom:
- *Size.*—Large. Average size when fully expanded—From 4 to 4½ inches.
- *Borne.*—Singly and several together.
- *Stems.*—Medium length; normal strength.
- *Form (when first open).*—Cupped. Permanence—Retains its form to the end.
- *Petalage.*—Double (full but open center); from 30 to 35 petals under normal conditions.
- *Color.*—Center of flower—Carmine, Plate 1, lightly overcast with Spectrum Red, Plate 1. Outer petals—Spectrum Red, Plate 1, lightly overcast with Scarlet Red, Plate 1. Base of petals (aiglet)—Picric Yellow, Plate 4. Inside of petals—Carmine, Plate 1, overcast with Spectrum Red, Plate 1. Reverse of petals—Spectrum Red, Plate 1, lightly overcast with Rose Red, Plate 12. General tonality from a distance—Carmine, Plate 1, lightly overcast with Spectrum Red, Plate 1.
- *Discoloration.*—General tonality at end of first day—Carmine, Plate 1, overcast with Spectrum Red, Plate 1. Second day—Carmine, Plate 1, lightly overcast with Spectrum Red, Plate 1. Third day—Spectrum Red, Plate 1, lightly overcast with Carmine, Plate 1.

Petals:
- *Texture.*—Thick; is not affected by wet or hot weather.
- *Appearance.*—Inside—velvety; outside—satiny.
- *Form.*—Oval; slightly notched.
- *Arrangement.*—Informal (with "rags" in center).
- *Petaloids in center.*—Few; small.
- *Persistence.*—Drop off cleanly.
- *Fragrance.*—Strong. Nature—"Old Rose" perfume (Centifolia).
- *Lasting quality.*—On the plant—long; as cut flower—long.

GENITAL ORGANS

Stamens, anthers: Large; many.
- *Arrangement.*—Regular around styles.
- *Color.*—Ochraceous-Orange, Plate 15.

Stamens, filaments (threads): Long. Color—Scarlet Red, Plate 1.

Pollen: Color—Pale Ochraceous Buff, Plate 15.

Styles: Columnar; uneven length; short; thin.

Stigmas: Color—Pale Lemon Yellow, Plate 4.

Ovaries: All enclosed in calyx.

Hips: None.

Seeds: None.

PLANT

Form: Climber.

Growth: Vigorous; upright; branching; shoots from 8 to 10 feet tall.

Foliage: 5 to 7 leaflets.
- *Size.*—Medium.
- *Quantity.*—Normal.
- *Color.*—New foliage: Upper side—Yellowish Oil Green, Plate 5, lightly overcast with Oxblood Red, Plate 1; under side—Oxblood Red, Plate 1, lightly overcast with Yellowish Oil Green, Plate 5. Old foliage: Upper side—Dark Cress Green, Plate 31; under side—Rainette Green, Plate 31.
- *Shape.*—Oval pointed.
- *Texture.*—Upper side—glossy; under side—smooth.
- *Ribs and veins.*—Ordinary.
- *Edge.*—Serrated (saw-toothed).
- *Serration.*—Both double and single; small.
- *Leaf stem.*—Color—Ivy Green, Plate 31. Under side—smooth.
- *Stipules.*—Long; smooth.

Wood:
- *New wood.*—Color—Light Bice Green, Plate 17. Bark—smooth.
- *Old wood.*—Color—Forest Green, Plate 17. Bark—smooth.

Thorn:
- *Thorns.*—Quantity: On main stalks from base—ordinary; on laterals from stalk—ordinary. Form—Flat base; medium length; some straight and some hooked downward. Color (when young)—Begonia Rose, Plate 1. Position—irregular.

*Prickles*—Quantity: On main stalks—none; on laterals—none.

*Short needles.*—Quantity: On main stalks—none; on laterals—none.

I claim:

A new and distinct variety of rose plant of the climber class, substantially as herein shown and described, characterized particularly as to novelty by the exceptionally large size of its flowers, the distinctive deep red color and the strong, Old Rose fragrance of its flowers, the vigorous habit of growth of the plant, and its glossy, dark green foliage.

No references cited.